United States Patent [19]

Bogdanov et al.

[11] Patent Number: 5,593,658
[45] Date of Patent: Jan. 14, 1997

[54] MEDICAL COMPOSITIONS

[75] Inventors: Alexei A. Bogdanov, Newton; Thomas J. Brady, Winchester, both of Mass.

[73] Assignee: The General Hospital Corporation, Boston, Mass.

[21] Appl. No.: 250,635

[22] Filed: May 27, 1994

Related U.S. Application Data

[63] Continuation of Ser. No. 940,590, Sep. 4, 1992, abandoned.

[51] Int. Cl.$^6$ ............................................. A61B 5/055
[52] U.S. Cl. ............ 424/9.34; 424/9.35; 424/9.36; 424/9.364; 514/6; 514/54; 514/59; 514/836; 436/173; 436/806
[58] Field of Search .................. 424/9, 4.5, 9.34, 424/9.35, 9.36, 9.364; 514/6, 54, 59, 836; 436/173, 806; 128/653.4, 654

[56] References Cited

U.S. PATENT DOCUMENTS

| | | | |
|---|---|---|---|
| 4,647,447 | 3/1987 | Gries et al. | 424/9 |
| 4,849,208 | 7/1989 | Stavrianopoulos | 424/1.1 |
| 5,069,216 | 12/1991 | Groman et al. | 128/653.4 |
| 5,094,848 | 3/1992 | Brixer | 424/85.91 |
| 5,141,739 | 8/1992 | Jung et al. | 424/4 |
| 5,160,725 | 11/1992 | Pilgrimm | 424/9 |
| 5,171,563 | 12/1992 | Abrams et al. | 424/1.1 |
| 5,208,324 | 5/1993 | Klaveness et al. | 534/16 |
| 5,213,788 | 5/1993 | Ranney | 424/9 |

FOREIGN PATENT DOCUMENTS

| | | |
|---|---|---|
| 0331616 | 9/1989 | European Pat. Off. |
| WO91/15753 | 10/1991 | WIPO |
| WO91/18630 | 12/1991 | WIPO |

OTHER PUBLICATIONS

Abuchowski et al., *J. Biol. Chem.*, 252:3578–81 (1977).
Abuchowski et al., *Bioch. Biophy. Acta.*, 578:41–46 (1979).
Abuchowski et al., *J. Biol. Chem.*, 252:3582–86 (1977).
Abuchowski and Davis, "Soluble Polymer–Enzyme Adducts," Ch. 13, *Enzymes as Drugs*, (Wiley, New York 1981).
Beauchamp et al., *Anal. Biochem.*, 131:25–33 (1983).
Chazov et al., *Thromb. Res.*, 12:809–816 (1978).
Chung–Ja et al., *Anal. Biochem.*, 165:114–127 (1987).
Duewell et al., *Invest. Radiol.*, 26:50–57 (1991).
Fujimoto et al., *Cancer*, 56:2404–2410 (1985).
Kennady et al., *Am. Surg.*, 33:763–771 (1967).
Manabe et al., *Biochem. Biophys. Acta*, 883:460–677 (1986).
Yokoyama et al., Macromol. Chem. 190:2041–2054, (1989).
Zalipsky et al., Polymeric Drugs and Drug Delivery Systems (1990) Ed: Dunn & Ottenbrite, pub: American Chemical Society.
Duncan, R., Polymers in Medicine (1984) Ed: Dusek, K. pub: Springer–Verlag.
Sawhney et al. Biomaterials 13(12):863–870, (1992).
Schmiedl, et al., *Invest. Radiol.*, 26:65–70 (1991).
Schumann–Giampieri et al., *Invest. Radiol.*, 26:969–974 (1991).
Torchilin et al., *J. Biomed. Mater. Res.*, 11:223–234 (1977).
Torchilin et al., *J. Biom. Mater. Res.*, 19:461–466 (1985).
Winding, O., *Neuroradiol.*, 21:123–126 (1981).
Wright et al., *Radiology*, 142:351–54 (1982).
Baxter et al., *Invest. Radiol.*, 26:1035–1040 (1991).
Nathan et al., *Bioconjugate Chem.* 4:54–62 (1993).
Sawhney et al., *Biomaterials*, 13(2):863–79 (1992) (Abstract Only).

*Primary Examiner*—Gary E. Hollinden
*Attorney, Agent, or Firm*—Fish & Richardson P.C.

[57] ABSTRACT

A biocompatible medical composition including a polymeric carrier, a protective chain linked to the polymeric carrier, and a reporter group linked to the carrier or to the carrier and the protective chain. The invention also relates to a method of treating a disease in a patient by administering to the patient a therapeutically effective amount of the composition, and may include scanning the patient using an imaging technique which can detect the reporter group to obtain a visible image of the distribution of the composition.

32 Claims, 9 Drawing Sheets

Scheme 1

Scheme 2

Scheme 3

■ - polyaminoacid

⋮⋮⋮ - polyoxyethyleneglycol

● - chelate

◉ - activated ester

▨ - protective group

MEDICAL COMPOSITIONS

This invention was made with Government support under Contract #RO1-CA-54886 awarded by the National Institutes of Health. The Government has certain rights in the invention.

This application is a continuation of 07/940,590 filed Sep. 4, 1992 now abandoned.

This invention relates to a biocompatible, macromolecular medical composition. The compositions may include therapeutic or diagnostic agents, have a prolonged blood half-life, low toxicity, and low immunogenicity, and can be detected by medical imaging techniques, e.g., magnetic resonance imaging for angiography, and as labels for targeted delivery.

BACKGROUND OF THE INVENTION

Contrast Agents for Magnetic Resonance Imaging

Accurate detection of abnormalities in a patient's body is an essential prerequisite for diagnosing and adequately treating disease. Visualization methods, e.g., magnetic resonance imaging (MRI), are becoming more important for such accurate detection. MRI is non-invasive and requires no exposure of humans to potentially harmful radiation. In MRI, tissues of different origin, such as normal and deviated, e.g., cancerous, tissues, may be differentiated on the basis of differences in relaxation times T1, the spin-lattice or longitudinal relaxation time, or T2, the spin-spin or transverse relaxation time. Because of these differences, differential signal intensity is produced which gives various degrees of contrast in MR images. The greater the difference in T1 or T2, the more pronounced the contrast. However, in many cases diseased or deviated tissue is isointensive, i.e., the diseased or deviated tissue has the same signal intensity as normal tissue, and is therefore not distinguishable from normal tissue without the use of special contrast agents.

Where MR imaging techniques employed to elucidate blood perfusion defects are based on the differentiation of flowing blood from stationary surrounding tissues, e.g., MR angiography (MRA). Three dimensional angiographic techniques, e.g., "Time of Flight" (TOF) and "Phase Contrast" (PC) techniques, provide detailed images of intracranial vessels. However, traditional MRA, i.e., Time of Flight MRA, is dependent on flow velocity and flow shape and thus high-quality angiography of peripheral vessels with high flow resistance is generally impossible due to an effect known as vessel saturation. To overcome this problem, contrast agents have been used to selectively lower the relaxation times of blood.

Gadolinium (III) diethylenetriamine pentaacetic acid (Gd-DTPA) dimeglumine is a widely used contrast agent which is relatively small (MW538) and extravasates on the first pass through the capillaries. However, the use of Gd-DTPA for MR angiography in all organs except the brain is limited, since the blood half-life of Gd-DTPA is less than 20 minutes, and the biological life in man of GD-DTPA is about 90 minutes. The extravasation results in a rapid decrease in vessel/muscle signal ratio, which makes the accurate detection of abnormalities and disease difficult. Moreover, Gd-DTPA dimeglumine, which is used in clinical practice, is immunogenic, which does not favor its repetitious administration to the same patient.

Similar problems occur with the use of ferrioxamine-B as a contrast agent. In addition, ferrioxamine-B causes a precipitous drop in blood pressure after its intravenous administration.

MRI contrast agents created using natural and synthetic macromolecules offer the advantage of high molecular relaxivity due to the multiple chelating groups coupled to a single polymer backbone. These groups can chelate paramagnetic cations, e.g., in Gd-DTPA-poly-1-lysine, or produce high relaxivity due to the presence of iron oxide, e.g., in iron-containing colloids. However, iron oxide-based colloids have their own ligand-independent specific site of accumulation in the body, e.g., the liver, spleen, and lymphoid tissues.

Chelating groups may be attached to a variety of natural polymers, e.g., proteins and polysaccharides, and synthetic polymers. Chemical attachment, e.g., by conjugation, of DTPA to bovine serum albumin will result in a macromolecular contrast agent, which is suitable for some applications, e.g., NMR-angiography, but because of the efficient recognition of modified albumin by macrophages, and albumin-receptors on endothelial cells this contrast agent has a short blood half-life. It is also immunogenic and toxic to reticuloendothelial system organs. Therefore, use for MR imaging is limited.

One way to diminish the antigenicity of albumin is to mask it with natural and synthetic polymers, e.g., spacer arms, by covalent attachment, but this leaves few reactive groups in the protein globule which are needed for binding the chelates and paramagnetic cations. Therefore, the use of such complexes in MR imaging is limited.

Synthetic polymers of 1-amino acids, such as poly-1-lysine (PL), are an alternative to modified natural proteins as backbones for contrast agents. PL modified with DTPA can be used as a radionuclide carrier for antibody-mediated targeting in nuclear medicine. Poly-1-lysine-DTPA, i.e., poly-1-lysine with DTPA groups bonded to epsilon-amino groups of lysine residues has been suggested as a Gd complexone, i.e., a compound which forms a complex with Gd, for use in MR angiography. It is also known that the toxicity of DTPA-poly-1-lysine is lower than that of DTPA-albumin. However, DTPA-moieties on DTPA-polylysine are recognized by liver Kupffer cells and some kidneys cells, presumably glomerulonephral phagocytes, which cause elevated and relatively rapid removal of the contrast agent from the blood. For example, 90% of the intravenously injected agent, e.g., poly-1-lysine-DTPA(Gd) (MW 48.7 kD), is removed from circulation in 1 hour ($t_{1/2}$=0.134 h) and accumulated in the kidneys, liver, and bone. Moreover, synthesis of DTPA-poly-1-lysine can be carried out with a cross-linking reagent, e.g., cyclic anhydride of DTPA. As a result, it is difficult to avoid the formation of cross-linked products of relatively high molecular weight and the preparation obtained is heterogeneous.

Nitrogen-containing polymers, e.g., polethyleneimine, have been modified with monofunctional derivatives of acetic acid to form a molecule where the backbone nitrogens and acetic acid residues are involved in complex formation with trivalent cations. However, because of extensive undesirable accumulation in the liver, paramagnetic complexes of polyethyleneiminoacetic acid are not widely used in MRI.

Polymeric contrast agents, e.g., starburst dendrimers, constitute a separate family of macromolecules with limited potential value as contrast agents. This family of agents has not been shown to be biocompatible and thus its value for in vivo imaging is limited.

Various polysaccharide-based chelating agents have been previously described; however, their activation complement which has been shown to be a feature of polysaccharides, preclude their extensive use in MR imaging.

Agents with Extended Blood Half-Life

Blood half-life and immunogenicity are crucial characteristics of any contrast agent designed for therapy or medical diagnosis. In some cases, such as enzyme-replacement therapy, fast elimination of therapeutic agents from circulation and accumulation in antigen-presenting cells limit their potential use in the treatment of disease. To overcome this problem, it has been suggested to chemically modify the macromolecular agents, e.g., enzymes, with various natural and synthetic polymers. Dextrans, synthetic polyamino acids, and polyethylene glycols are used most frequently. However, only polyethylene glycol (PEG) and its monomethyl ester (MPEG) are suitable to prolong blood half-life and simultaneously decrease the immunogenicity of the therapeutic agent. The reason for modifying antigenic determinants by MPEG may be explained by the screening of electrostatic charge of the protected micromolecule, e.g., protein, and by the ability to form numerous bonds with water in solutions.

About three molecules of water are associated with each ethylene oxide unit and form the immediately adjacent water microenvironment for the polymer. This prevents, to a great extent, the adsorptive interactions of proteins and cells with PEG chains. The use of PEG in its activated forms, e.g., 4,6-dichloro-s-triazine-activated PEG or MPEG, is undesirable for protein modification, because the activated product is contaminated with by-products and is highly moisture-sensitive. Stable and virtually non-biodegradable biodegradable bonds have been formed by the conjugation of MPEG, e.g., reacting 4,6-dichloro-s-triazine and 1,1'-carbonyldiimidazole with aminogroups.

PEG and MPEG are used in contrast agents for medical imaging. Covalent modifications of desferrioxamine-B with MPEG improve the body's tolerance of such contrast agents in vivo, but does not result in any significant change in imaging efficacy. Contrast agents containing MPEG or PEG as a component of paramagnetic mixtures or in cross-linked paramagnetic polymers also have been used.

Targeted Contrast Agents

Contrast agents targeted to the sites of interest help to increase the effectiveness of MR imaging methods. Such diagnostic agents may include combinations of a ligand and a paramagnetic contrast agent coupled by strong interaction, e.g., a covalent chemical bond. After systemic application, such a contrast agent accumulates in the target site which is determined by ligand specificity. As a result, the site of accumulation is easily differentiated from surrounding tissue because it appears hyper- (or hypo-) intensive on MR images. The ligand which directs the contrast agent to the target site may be specific to receptors on either normal or transformed cells of a given organ or tissue. In the first case the contrast agent will be accumulated in normal tissue; in the second case, it will be accumulated in altered tissue.

Success in designing a targeted contrast agent is mainly determined by the following properties: 1. avidity to target site; 2. antigenicity, i.e., ability to pass through capillary endothelium; and 3. blood half-life of the ligand or targeting ("vector") molecule. Coupling a contrast agent to a targeting ligand molecule, e.g., an antibody or its fragments, which creates a targeted contrast agent, e.g., a chelated paramagnetic cation, paramagnetic colloid or combination of a chelate and a paramagnetic colloid conjugated to a targeting molecule, typically decreases its potential value for any of a number of reasons, e.g., decreased avidity to a target site, increased antigenicity, or decreased half-life. For example, coupling of a small antibody fragment, e.g., a Fab or Fv chimeric molecule, to a large paramagnetic molecule, e.g., DTPA-polymer, or a superparamagnetic colloid, e.g., iron oxide, to form a targeted contrast agent will increase the immune response of the recipient organism to the agent because of the adjuvant properties of the agent itself. The paramagnetic molecule or colloid itself may be recognized by the recipient organism's opsonizing proteins and the contrast agent may be trapped in reticuloendothelial system organs. As a result, the contrast agent is removed from the circulation by the liver and spleen before any substantial concentration is achieved in the target site. Moreover, such a contrast agent may be recognized as a foreign antigen which may give rise to undesirable host antibodies.

SUMMARY OF THE INVENTION

The invention features a biocompatible medical composition including a polymeric carrier, a protective chain linked to the polymeric carrier, and a reporter group linked to the carrier or to the carrier and the protective chain. The polymeric carrier may be chosen from the group of polyamino acids, polyethyleneimines, natural saccharides, aminated polysaccharides, aminated oligosaccharides, polyamidoamine, polyacrylic acids, or polyalcohols.

The invention also features a composition having the formula:

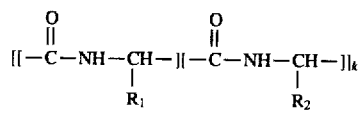

wherein the

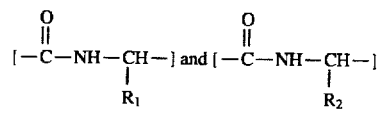

groups can be linked in any order, e.g., the $R_1$ unit can be repeated several times in the chain before an $R_2$ unit occurs, and vice versa; wherein k is 100–560; $R_1$ is $(CH_2)_4NHCO(CH_2)_nCOOCH_2CH_2A—B—OR_3$, where n is 2–6; A is $[OCH_2CH_2]_x$, where x is 15–220; B is $[OCH_2CH_2]_x$ or $[OCH(CH_3)CH_2]_y$, where y+x is 17–220; $R_2$ is a chelating group; and $R_3$ is H, $(CH_2)_pCH_3$ or $(CH_2)_pCOOH$, and p is 0–7.

In this composition, the chelating group may be, e.g., diethylenetriamine pentaacetic acid, 1,4,7,10,-tetraazacyclododecane-N,N',N",N"'-tetraacetic acid, 1,4,7,10,-tetraazacyclododecane-N,N',N"-triacetic acid, ethylene-bis(oxyethylenenitrilo)tetraacetic acid, or ethylenediaminetetraacetic acid.

The polyamino acid of the composition preferably has 20–560 amino acid units, a molecular weight of 1,000–100,000 daltons, and is preferably non-proteinaceous. The polyamino acid may be a polymer of a single species, or at least two different species of amino acid, or may be a block copolymer.

The polyamino acid may include polyamino acid fragments linked by cleavable bonds, e.g., S—S bonds. In particular, the polyamino acid may be, e.g., poly-l-lysine, poly-d-lysine, poly-alpha,beta-(2-aminoethyl)-D,L aspartamide, or poly-l-aspartic acid.

The protective chain of the composition may be, e.g., polyethylene glycol, methoxypolyethylene glycol, methoxypolypropylene glycol, a copolymer of polyethylene glycol, methoxypolyethylene glycol, or methoxypolypropylene glycol, or derivatives thereof. In addition, the protective chain may be a block copolymer of polyethylene glycol and one of the group of polyamino acids, polysaccharides, polyamidoamines, polyethyleneamines, or polynucleotides. The protective chain may also be a copolymer of polyethylene glycol including a monoester of a dicarboxylic acid. The protective chain preferably has a molecular weight of 500–10,000 daltons.

The reporter group may be a complexone, e.g., a chelating group. The chelating group may be, e.g., diethylenetriaminepentaacetic acid, triethylenetetraminehexaacetic acid, ethylenediamine-tetraacetic acid, 1,2-diaminocyclo-hexane-N,N,N',N'-tetra-acetic acid, N,N'-Di(2-hydroxybenzyl) ethylenediamine, N-(2-hydroxyethyl) ethylenediaminetriacetic acid, nitrilotriacetic acid, ethylene-bis(oxyethylene-nitrilo) tetraacetic acid, 1,4,7,10,-tetraazacyclodo-decane-N,N',N"N"'-tetraacetic acid, 1,4,7,10,-tetraaza-cyclododecane-N,N',N"-triacetic acid, 1,4,7-tris(carboxymethyl)-10- (2'-hydroxy)propyl) -1,4,7,10-tetraazocyclodecane, 1,4,7-triazacyclonane-N,N',N"-triacetic acid, or 1,4,8,11-tetraazacyclotetra-decane-N,N',N"N"'-tetra-acetic acid.

The composition may further include an alfa-, beta-, or gamma-emitting radionuclide linked to the complexone. The radionuclide may be gallium 67, indium 111, technetium 99 m, chromium 51, cobalt 57, molibdenium 99, or a molecule linked to an iodine isotope.

The reporter group may also include a diagnostic agent, e.g., a contrast agent, which may include a paramagnetic or superparamagnetic element, or a combination of a paramagnetic element and a radionuclide. The paramagnetic element may be chosen from the group of transitional metals or lanthanides having atomic numbers 21–29, 42, 44, or 57–71. The paramagnetic element may be, e.g., gadolinium (III), dysprosium (III), holmium (III), europium (III), iron (III), or manganese (II).

The invention also features a composition in which the reporter group includes a therapeutic agent such as a cytostatic, antibiotic, hormonal, analgesic, psychotropic, antiinflammatory, antiviral, or antifungal drug, or a lymphokine.

The composition may further include a targeting group linked to the polymeric carrier or the protective chain or both. The targeting group may be an antibody, fragment of an antibody, chimeric antibody, enzyme, lectin, or saccharide ligand.

The composition may also include a reporter group which is a particle, colloidal particle, or a colloidal precipitate. The colloidal precipitate may include an oxide, sulfide, or hydroxide of a transitional element, or lanthanide having atomic numbers 21–29, 42, 44, or 57–71. The reporter group may also be a silicon oxide colloid or polymer containing silicon, sulfur, or carbon, or a fluorine-containing molecule, e.g., a fluorocarbon.

The reporter group may also be a pyridyldithioacyl group, e.g., a N-(2-pyridyldithio)propionyl group, N-hydroxysuccinimidyl, N-hydroxysulfosuccinimidyl, imidazolyl, benzotriazolyl, aminoalkyl, aldehyde, thioalkyls, thiolane, haloid acyl, haloid alkyl, or haloid phenyl, or a diazo- or hydrazo-group, e.g., a 4-hydrazionoxyethyl, 4-hydrazinobenzyl, diasirinyl, azidophenyl, or azidoalkyl group.

In addition, the invention features a method of preparing the composition by linking the polymeric carrier with the protective chain to produce a protected carrier, and then linking the protected carrier with the reporter group. If the protective chain includes a methoxypolyethylene glycol analog, linking the polymeric carrier with the analog produces a semi-stable gel. The method may further include linking a targeting group to the carrier, protective group, or both.

The invention also features a method of treating a disease in a patient by administering to the patient a therapeutically or diagnostically effective amount of the composition of the invention. The method may further include scanning the patient using an imaging technique which can detect the reporter group to obtain a visible image of the distribution of the composition. The administration may be by intravascular or intraperitoneal injection, and the imaging technique may be, e.g., magnetic resonance imaging, nuclear medicine imaging, position emission tomography, or single-photon-emission computed tomography.

In particular applicant's composition allows very small dosages of a paramagnetic element, e.g., gadolinium, to be administered to a patient and still obtain excellent images, e.g., MR images. For example, the reporter group may include gadolinium supplied at a dosage of less than 0.05 mmol Gd/kg of body weight of the patient. Preferably, the dosage is about 0.02 to 0.04 mmol Gd/kg of body weight.

The invention also features a method of treating a patient by scanning a submillimeter vessel of the patent to obtain a visible image of the submillimeter vessel. A submillimeter vessel is one that has an inner diameter of less than one millimeter.

As used herein, the term "linked" means covalently and non-covalently bonded, e.g., by hydrogen, ionic, or Van-der-Waals bonds. Such bonds may be formed between at least two of the same or different atoms or ions as a result of redistribution of electron densities of those atoms or ions.

A "polymeric carrier" is a molecule comprised of several linked chemical moieties which may be the same or different, and serves as a site where a reporter group is linked and is shielded by protective chains.

A "protective chain" is a molecule(s) which protects a carrier molecule and a reporter group from contact with other macromolecules due to extensive linking of water to the chains.

A "complexone" is a molecule or several molecules or chemical radicals or moieties which constitute a favorable environment for linking an ion (a cation or an anion). Dissociation of the ion from the environment is hindered due to kinetic or/and thermodynamic stability of linking.

A "chelating molecule" or "chelate" is a complexone which links cations.

A "reporter group" is an atom, ion, molecule, or complexone that may be linked to a polymeric carrier or protective chain to produce an effect which is detectible by any methods of chemical, physical or biological examination, or by any means of medical examination of a patient. A reporter group may be a therapeutic or diagnostic agent.

The terms "derivative" or "analog" as used herein mean a compound whose core structure is the same as, or closely resembes that of, a parent compound, but which has a chemical or physical modifaction, such as a different or additional side groups; the term inclues copolymers of parent compunds that can be linked to other atoms or molecules.

The terms "ligand", "targeting group" or "vector molecule" mean any atom, ion, or molecule linked to a carrier and/or to a protective chain and/or to a reporter group to increase the accumulation of the composition in a target site of an organism to a greater degree through the targeting group were absent.

The term "polyamino acid fragment" means individual amino acid radicals or several linked amino acids which may be linked to form a polyamino acid.

A "semi-stable gel" is a gel which forms a liquid phase by standing, or when temperature, pH or other conditions are varied.

The term "vessel mapping" refers to obtaining an image of a vessel or vessels where spatial orientation and delineation of vessels may be elucidated.

The term "aminated" describes molecules including linked amino groups.

A "diagnostically effective amount" of the composition is an amount that will provide an image of the composition in the patient.

A "therapeutically effective amount" of the composition is an amount that will provide a therapeutic benefit to the patient.

Some important features of the compositions of this invention which make them surprisingly suitable for MR imaging include: 1) the ability to chelate paramagnetic cations to achieve a high molecular relaxivity, which is essential for its use as an NMR contrast agent 2) an extended blood half-life 3) low toxicity and 4) non-immunogenicity.

This invention also provides the advantages of only having to administer one dose of the contrast agent, along with enhanced signal/noise ratios in the diagnostic images obtained.

The following properties are common for the compositions of the invention: 1) increased relaxivity of each paramagnetic cation compared to Gd-DTPA, 2) large numbers of chelating groups on each molecule, 3) enhanced blood pool concentration after intravenous injection, 4) enhanced sites of abnormal endothelial permeability, and 5) prolonged circulation time compared to Gd-DTPA.

Other features and advantages of the invention will be apparent from the following description of the preferred embodiments and from the claims.

DETAILED DESCRIPTION

Drawings FIG. 1 is a diagram of three schemes for synthesizing the compositions of the invention.

Figure 9:

FIG. 9 an MR image of two rats in 3-D bright-pixel reconstruction after an intravenous injection of MPEG(MW 5kD)-poly-l-lysine(MW 25 kD)-DTPA(Gd) (left image) and gadopentate dimeglumine (right image).

Figure 10B:
Figure 10A:

FIGS. 10a and 10b bare of MR images of a rabbit in 3D bright-pixel reconstruction of the lateral (FIG. 10a) and cranio caudal projection (See FIG. 10b) after an intravenous injection of MPEG (MW 5 kD)-poly-l-lysine(MW 25 kD)-DTPA(Gd).

Figures 11A, 11B:
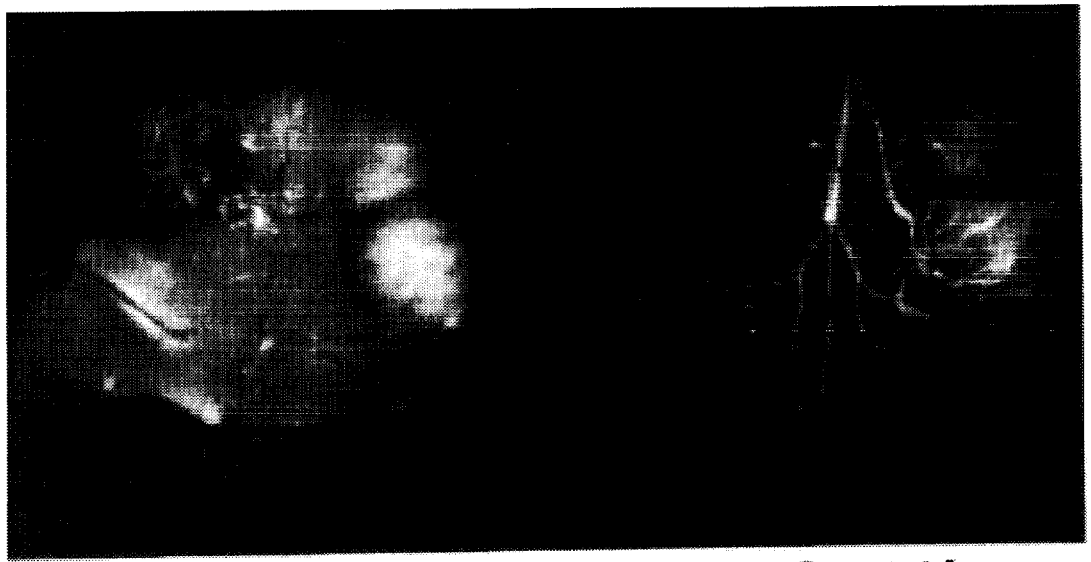

FIGS. 11a and 11b are MR images of the left flank and thigh of a rat in 3-D bright-pixel reconstruction before (FIG. 11a) and after (FIG. 11b) an intravenous injection of MPEG (MW 5 kD)-poly-l-lysine(MW 25 kD)-DTPA(Gd). Images were taken two weeks after injection of R3230 mammary adenocarcinoma cells into the left flank of the rat.

STRUCTURE OF THE COMPOSITION

The compositions of this invention include a single chemical entity including a polymeric carrier, a protective chain linked to polymeric carrier, and a reporter group. For example, the composition may have the following formula:

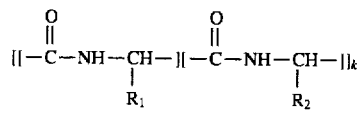

wherein said

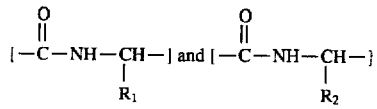

groups can be linked in any order; wherein k is 100–560; $R_1$ is $(CH_2)_4NHCO(CH_2)_nCOOCH_2CH_2A$—B—$OR_3$, where n is 2–6; A is $[OCH_2CH_2]_x$, where x is 15–220; B is $[OCH_2CH_2]_x$ or $[OCH(CH_3)CH_2]_y$, where y+x is 17–220; $R_2$ is a chelating group; and $R_3$ is H, $(CH_2)_pCH_3$ or $(CH_2)_pCOOH$, and p is 0–7.

Polymeric carriers

The polymeric carrier may be chosen from polyamino acids, e.g., linear or branched polymers of a single amino acid species or of different amino acid species, e.g., regular or statistic block-copolymers of polyamino acids, e.g, preferably linear poly-l- or poly-d-lysine, poly-alpha, beta-(2-aminoethyl)-d,1-aspartamide, or poly-l-aspartic acid.

The molecular weight of the polyamino acid carrier is preferably between 1,000 and 100,000 Daltons. Polyamino acids with narrow molecular weight (MW) distributions are preferred to those with broad MW distributions. The polyamino acids are linked with peptide bonds or, when obtained by condensation of two or more polyamino acid fragments or individual amino acids with cleaveable bonds, e.g., S—S bonds, which may be cleaved in vivo. Polyamino acids may be natural or synthetic, are preferably nonproteinaceous, and are prepared by chemical synthesis or by recombinant techniques, such as genetic engineering.

The polymeric carrier also may be comprised of polyethyleneimines, e.g., branched amino-containing polymers or carboxylated polyethyleneimines, i.e., reacted with derivatives of carbonic acids; natural saccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups.

Such oligosaccharides may be obtained by chemical alteration of, e.g., dextran, mannan, xylan, pullulan, cellulose, chytosan, agarose, fucoidan, galactan, arabinan, fructan, fucan, chitin, pustulan, levan or pectin. In addition these polysaccharides or oligosaccharides may be heteropolymers or homopolymers of monosaccharides, e.g., glucose, galactose, mannose, galactose, deoxyglucose, ribose, deoxyribose, arabinose, fucose, xylose, xylulose, or ribulose, The polymeric carrier may be a linear, branched or dendrimeric polyamidoamine; polyacrylic acid; polyalcohols, e.g., polyvinylalcohol and polyxylitol to which carboxylic or amino groups are chemically linked; or oligonucleotides Protective Chains The protective chain may be PEG, preferably esterified by dicarboxylic acid to form a polyethylene glycol monoester; MPEG, methoxypolypropylene glycol or a copolymer thereof, preferably in the form of an ester with dicarboxylic acid, polyethylene glycol-diacid, polyethylene glycol monoamine; MPEG monoamine; MPEG hydrazide; MPEG imidazolide, and derivatives of all of the above.

In addition, the protective chain may be a block-copolymer of PEG and a polymer, e.g., of polyamino acids, polysaccharides, polyamidoamines, polyethyleneamines or polynucleotides (as described above under polymeric carriers). The blocks are preferably alternated to give a linear block-copolymer. The overall molecular weight of the protective chain is preferably 500 to 10,000 Daltons. The protective chain is preferably linked to the polymeric carrier by a single bond.

Reporter groups

The reporter groups of the invention are preferably linked to a polymeric carrier but also may be linked to a protective chain. The reporter groups include complexones, e.g., chelating molecules such as
diethylenetriamine-pentaacetic acid (DTPA),
triethylenetetraminehexaacetic acid (TTHA),
ethylenediaminetetraacetic acid (EDTA),
1,2-diaminocyclohexane-N,N,N',N'-tetraacetic acid,
N,N',-Di(2-hydroxybenzyl)ethylenediamine (HBED),
N-(2-hydroxyethyl)ethylenediaminetriacetic acid,
nitrilotriacetic acid,
ethylene-bis(oxyethylenenitrilo)tetraacetic acid (EGTA),
1,4,7,10,-tetraazacyclododecane-N,N',N'',N'''-tetraacetic acid (DOTA),
1,4,7,10,-tetraazacyclododecane-N,N',N''-triacetic acid (DO3A),
1,4,7-tris(carboxymethyl)-10-(2'-hydroxy)propyl)-1,4,7,10-tetraazocyclodecane (HP-DO3A),
1,4,7-triazacyclonane-N,N',N -triacetic acid (NOTA),
1,4,8,11-tetraazacyclotetradecane-N,N',N'',N'''-tetraacetic acid (TETA), preferably DOTA and DTPA, where these chelating molecules preferably include a contrast agent, e.g., a paramagnetic cation and/or radionuclide.

The paramagnetic elements, e.g., cations, include transitional metals or lanthanides, e.g. elements with atomic numbers 21–29, 42, 44, 57–71, preferably gadolinium (III), dysprosium (III), holmium (III), europium (III), iron (III), or manganese (II).

The radionuclides include alfa-,beta- and gamma-emitters, preferably gallium 67, indium 111, technetium 99 m, chromium 51, cobalt 57, molibdenium 99, molecules, e.g., tyrosine and p-oxybenzoic acid, linked to isotopes of iodine, e.g., iodine 131.

The reporter group may also include fluorine-containing molecules, e.g., fluorocarbons.

The reporter group may also include therapeutic agents, e.g., cytostatics, antibiotics, hormones, e.g., growth factor, analgesics, psychotropic, antiinflammatory, antiviral, antifungal drugs or lymphokines, e.g., interleukin 2. The therapeutic agents are preferably linked to a carrier with detachable or semistable bonds.

The reporter group may also include a particle, or colloidal particle, or colloidal precipitate of oxides, sulfides and/or hydroxides of transitional elements and lanthanides with atomic numbers 21–29, 42, 44, 57–71, or silicon oxide colloids or polymers containing silicon or polymers of atoms of sulfur, carbon, or silicon. The particle or particles may be contained as an integral part of, or may be surrounded by, a semi-permeable membrane.

The compositions may also include additional reporter groups which may be chosen from $(CH_2)_pCOOH$, where p is between 0 and 7; pyridyldithioacyl groups, e.g., N-(2-pyridyldithio)propionyl groups; N-hydroxysuccinimidyl, N-hydroxysulfosuccinimidyl, imidazolyl, benzotriazolyl, aminoalkyl, aminoacyl, aldehyde, thioalkyls, thiolanes, haloid acyl, haloid alkyl, or haloid phenyl; diazo- and hydrazo-, e.g. 4-hydrazinoxyethyl, 4-hydrazinobenzyl, diazirinyl, azidophenyl, or azidoalkyl groups.

The above groups are linked to the polymeric carrier and/or to the protective chains, and are needed for conjugating or linking other ligands, e.g., a targeting group, capable of interacting with cell surface receptors, proteoglycans, adhesion molecules, ion channels or enzymes, to the compositions of this invention.

Targeting Group

The targeting group may include antibodies; fragments of antibodies; chimeric antibodies, where said antibodies are polyclonal or monoclonal; enzymes; quasi substrates of enzymes; lectins; or saccharide ligands of lectins detachably or nondetachably linked to the composition.

Synthesis of the composition

Figure 1:
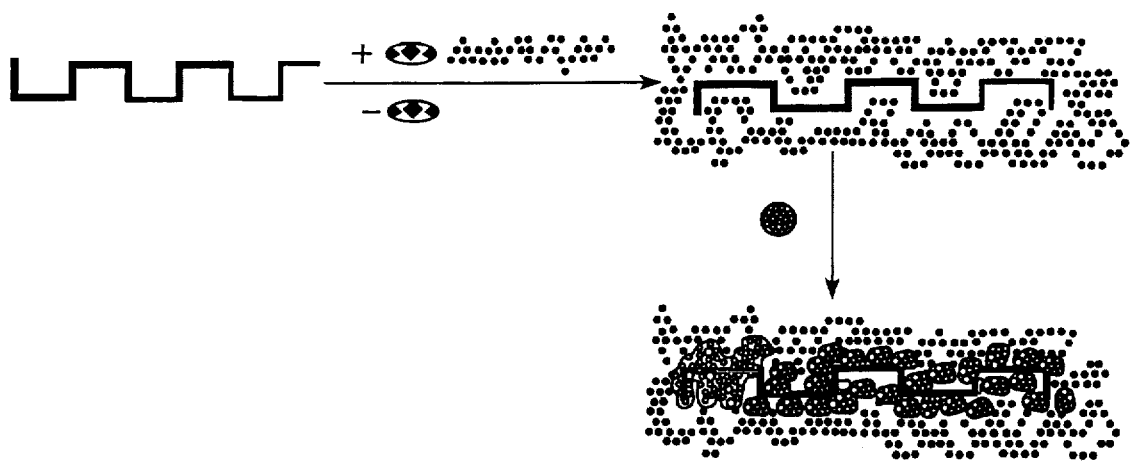
Figure 1:
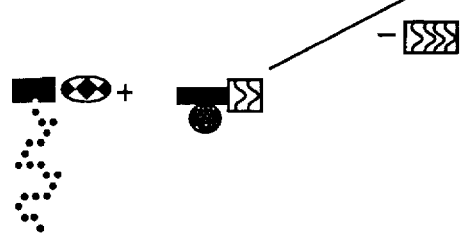
Figure 1:
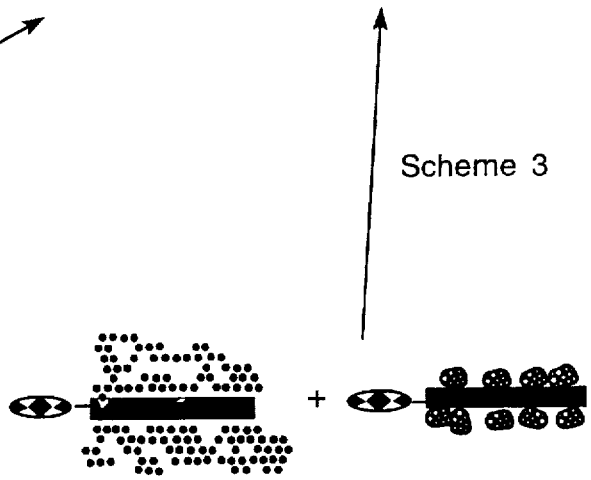

The compositions of this invention may be synthesized using any one of the following methods (See FIG. 1). An example of synthesis using poly-l-lysine as a polymeric carrier, MPEG as a protective chain, and a complexone as a reporter group is provided. This synthetic composition is especially suitable as a macromolecular contrast agent.

Scheme 1

The compositions may be prepared in two stages by first reacting polyamino acid with activated MPEG analogs, and then reacting this reaction mixture with an activated chelating compound. This procedure is preferred when poly l-lysine is used as the polymeric carrier (See FIG. 1).

ε-amino groups of poly-l-lysine were reacted with activated derivatives of carboxylated MPEG, e.g., acid chlorides, anhydrides, mixed anhydrides, nitrenes, isothiocyanates and imidazolides, and activated esters, e.g hydroxysuccinimide, hydroxysulfosuccinimide, p-nitrophenyl, benzotriazolide.

The chelating molecule is brought into reaction with the remaining amino groups, either in activated form, e.g., anhydride, mixed anhydride, or isothiocyanate, or in a non-activated form. If the chelating molecule is in the non-activated form, it is activated to obtain an activated ester in the presence of succinimide or sulfosuccinimide and carbodiimide and is then brought into reaction with the remaining amino groups. The reaction may be preceded with an additional chemical modification of the polyamino acid backbone or MPEG chains which are not limited to reactions resulting in the formation or elimination of at least one chemical bond.

The sequence of chemically linking the protective chains and a reporter group to a polymeric carrier may be reversed, i.e., linking of a reporter group preceeds linking of protective chain(s) to the polymeric carrier, but preferably, the reporter group is used as a monofunctional activated analog, i.e., one molecule of activated reporter group forms only one covalent linkage with a polymeric carrier.

Scheme 2

The compositions also may be synthesized using standard peptide synthesis protocols with modified amino acid precursors such as MPEG-amino acid and complexone-amino acid. In this case, moieties of complexone and PEG may be alternated in a controllable manner.

Scheme 3

Oligomers of PEG-polyamino acids may be conjugated with oligomers of complexone-amino acids to form a block-copolymer.

All three schemes will result in predictable compositions with highly predictable molecular weight distributions.

When carboxylated carriers are used, such as carboxylated saccharides, or polyaminoacids with carboxy groups in their radicals, such as poly-l-aspartic acid, the polymeric carrier is preferably activated in the presence of carbodiimide and sulfosuccinimide, as described in Example 2 for DTPA, and then reacted with aminated protective chains, such as MPEG monoamine at pH 7–9. The linking of complexone or chelate is then achieved preferably by carbodiimide condensation.

When used for medical imaging, the compositions of this invention preferably have a non-proteinaceous polyamino acid molecule serving as a carrier of covalently attached activated analogs of linear or branched chelating molecules, to which a MR reporter cation is linked, i.e., ionically chelated. The carrier forms a single chemical entity with protective chains of MPEG.

The synthetic route of preparing the compositions of this invention includes covalent modification of the polyamino acid carrier. Conjugation of 1,1'-carbonyldiimidazole-treated MPEG to aminogroups requires high excesses of the modifier, e.g., activated MPEG, which leads to the formation of semi-stable gels since the solubility of polyamino acids in the presence of MPEG is reduced. The procedure for preparing N-hydroxysuccinimidyl MPEG-succinate described in Scheme 1 gives a product with a highly activated ester content, e.g., greater than 75%, which is advantageous for preparing the compositions of this invention. Special purification of intermediates enables elimination of peroxides and yields a preparation for in vivo use.

Linking MPEG to the polymeric carrier, e.g., polyamino acid, also prevents possible cross-linking of the poly-amino acid with the cyclic anhydride of DTPA. MPEG chains prevent the formation of by-products because they create a steric barrier for cross-linking the reagent. Therefore, the formation of high-molecular weight products can be controlled, which makes the synthetic steps predictable. As a result, a homogenous preparation is obtained with a narrow molecular weight distribution.

The polymeric carriers preferably contain peptide bonds. The same bonds are involved in conjugating a chelating molecule with reactive groups of the amino acid radicals. The compositions, therefore, are potentially biodegradable by various animal non-specific peptidases. To assist in vivo elimination of polymeric carrier and protective chains together with a reporter group, or to enhance dissociation of a reporter group from the carrier to the biological milieu if such a reporter group is a therapeutic agent, elements of polymeric carrier or protective chains or reporter groups could be linked together by a semistable linkage, such as S—S bonds. Small amounts of trapped compositions may be removed from the body by degradation to smaller fragments. However, a variety of activated PEG derivatives may be used for the preparation of the compositions thus making them either virtually undegradable or, on the contrary, labile. However, labile compositions are undesirable, since detaching MPEG will result in more extensive accumulation of the contrast agent compositions in the reticuloendothelial system.

The use of the compositions of this invention in MR imaging requires the presence of an MR reporter group, such as a paramagnetic cation, e.g., gadolinium (III). The transchelation technique developed for this experiment is based on an embodiment of Harris et al., *J. Polym. Sci.*, 22:–341–52, which is incorporated herein by reference. Applicants used Gd-citrate to prevent the contact of the contrast agent with gadolinium oxides, used previously by Griess et al., U.S. Pat. No. 4,647,447, or gadolinium chloride, used previously by Bardy et al. U.S. Pat. 4,804,529. The gadolinium citrate easily forms contaminants such as colloidal hydroxides at pH values greater than 6.5, which is within the range of optimal pH values for the NMR contrast agents of this invention. The addition of a special purification step, e.g., an anion-exchange chromatography step, allows the separation of Gd-labeled MPEG-PL-DTPA (Gd) from possible anionic contaminants, e.g., MPEG-PL-DTPA(Gd) with a low degree of substitution of amino groups with MPEG or small amounts of PL-DTPA(Gd).

The protective chains, e.g., MPEG, of this invention do not react with the C3 component of complement which is a distinct advantage over previously known agents, e.g. dextran-DTPA(Gd), which are known to react with the C3 component of complement.

MPEG prevents the exposure of chelating groups and paramagnetic cations to receptor cells, e.g., glomerulonephral phagocytes, capable of recognizing them. MPEG also forms a steric barrier which prevents rechelation of Gd cations by serum proteins such as transferrin. The compositions of this invention also prevent possible delayed toxic effects of re-chelated gadolinium.

MPEG conjugation lowers the toxicity of the composition of this invention by preventing significant accumulation of the chelating polymer in the liver and spleen. Acute toxicity studies of the compositions of this invention have indicated no apparent toxicity in mice at concentrations exceeding 10–35 times the optimal doses. Histological examination of tissues of these mice have shown no deviations from control animals.

Figure 2:
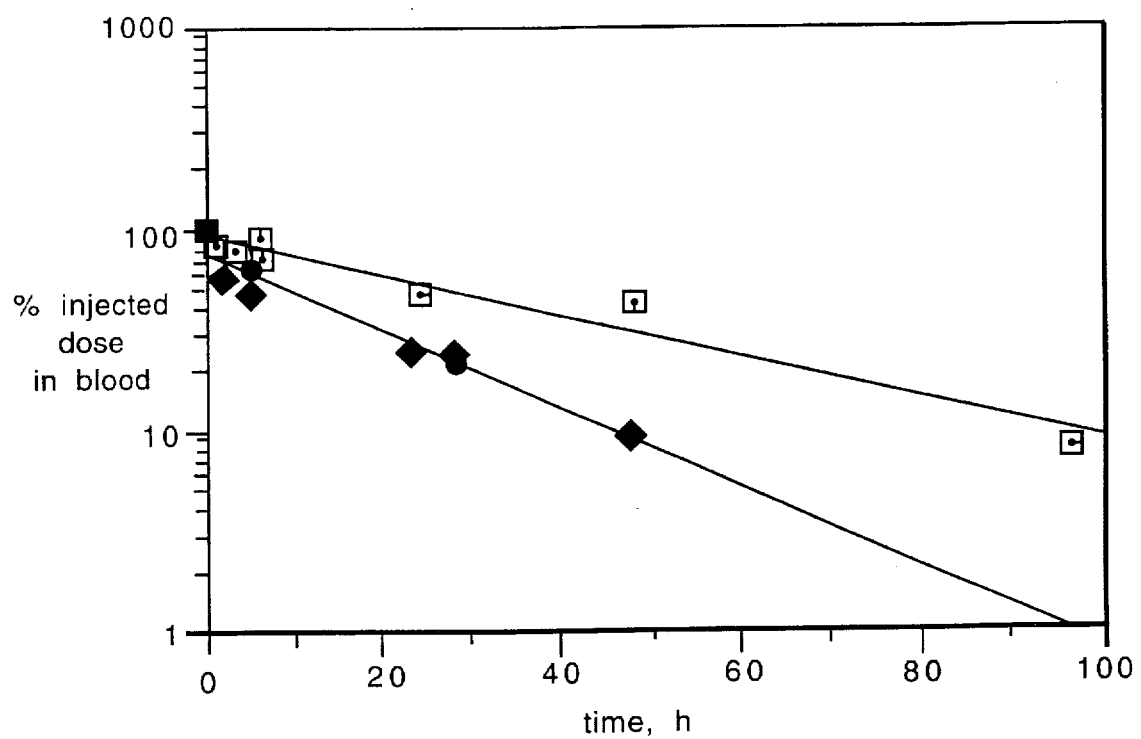
FIG. 2 is a graph of the blood clearance of [$^{111}$In]-labeled and Gd-saturated MPEG(MW 5 kD)-poly-l-lysine(MW 53.5 kD)-DTPA (squares) and MPEG(MW 2 kD)-poly-l-lysine(MW 41 kD )-DTPA (diamonds).

The blood half-life of the compositions of the invention was determined in rats. The radioactive and paramagnetic contrast agents were incorporated into the composition prepared according to Examples 1 and 3 in order to accurately determine its pharmacokinetic characteristics in vivo. The rats were visualized at different time points using a gamma camera to follow the distribution of the composition. As indicated by the data presented in FIG. 2, the blood half-life of the disclosed contrast agent was equal to 24 hours for MPEG(MW 5 kD)-poly-l-lysine(MW 53.5 kD)-DTPA labelled with [$^{111}$In] and saturated with gadolinium, while a smaller contrast agent MPEG(MW 2 kD)-poly-l-lysine (MW 25 kD)-DTPA labelled with [$^{111}$In] and saturated with gadolinium, was removed from the blood at a faster rate with the $t_{1/2}$ being 6 hours. The only two sites in the body where accumulation of these compositions was detected in quantities significantly larger than 1% of injected dose per gram of tissue, were the spleen and kidneys. However, the total amount of contrast agent entrapped in both kidneys and spleen did not exceed about 7% of the contrast agent in the composition.

Figure 3:
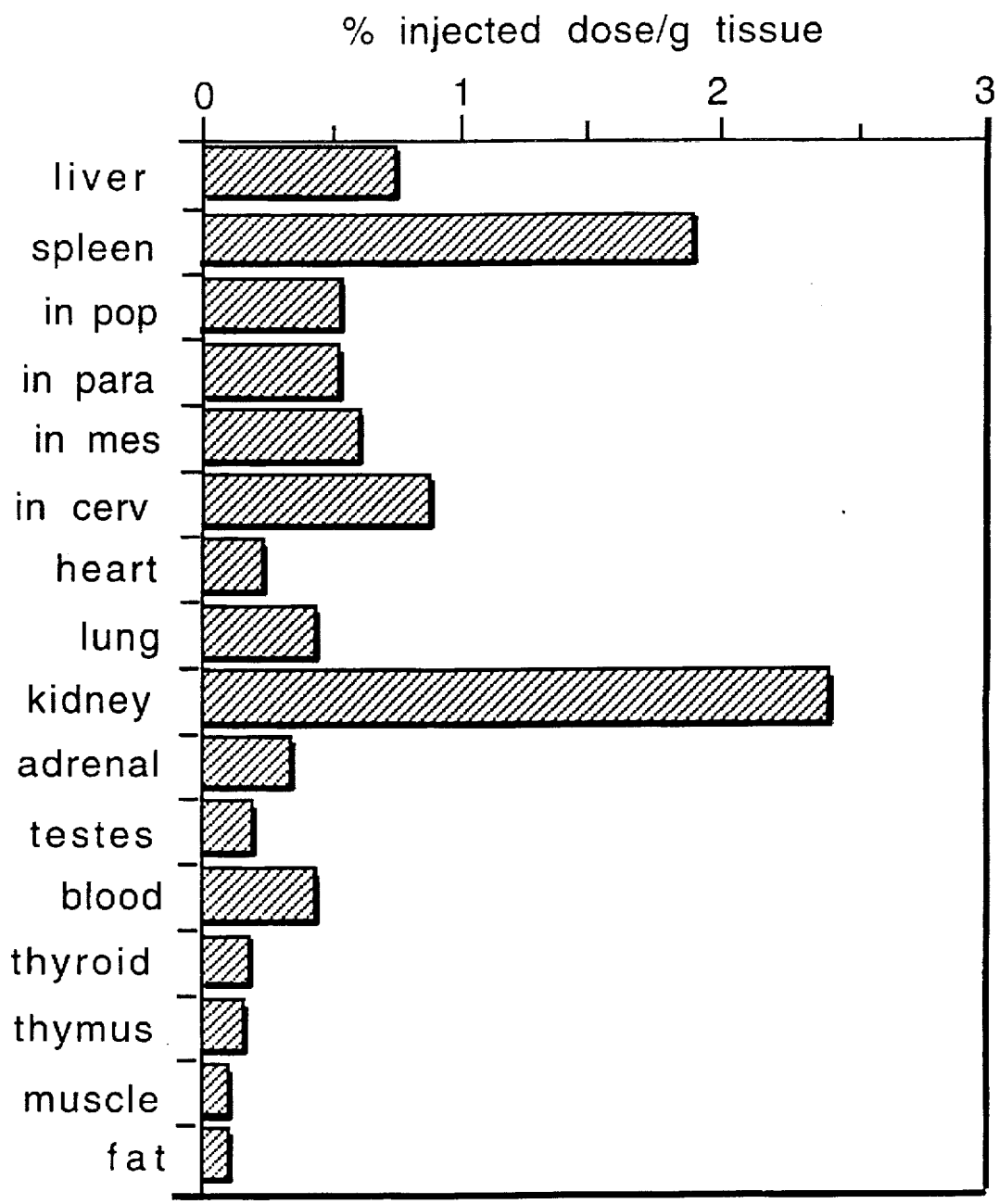
FIG. 3 is a graph of the biodistribution of [$^{111}$In]-labelled and Gd-saturated MPEG(MW 5 kD)-poly-l-lysine(MW 53.5 kD)-DTPA 90 hours after intravenous injection.

The typical biodistribution 90 hours post-injection of MPEG(MW 5 kD)-poly-l-lysine(MW 53.5 kD)DTPA, labelled with [¹¹¹In] and saturated with gadolinium is presented in FIG. 3. The total amount of the composition retained in the liver, spleen and both kidneys totaled 15–18% after 90 hours in circulation. The above data indicates that the contrast agents of this invention do not accumulate in the reticuloendothelial system of animals after intravenous injection in significant amounts and may be removed from circulation, presumably by degradation in the blood, through bile excretion, and by kidney filtration.

Immunogenicity

Prevention of the interaction of the reporter group with plasma proteins by MPEG chains hinders the binding of the compositions with cells capable of opsonin recognition, e.g., antigen presenting phagocytes, and with immunocompetent blood cells, e.g., resting B-cells. As a result, the formation of an immune response to the reporter group itself is unlikely and the production of host antibodies to the reporter group is largely avoided. This enables the repetitious use of the composition of this invention if necessary. The immune response of animals to intravenous injections of the compositions of this invention have detected no antibody formation to PEG and acetylated polyamino acid.

Figure 4:
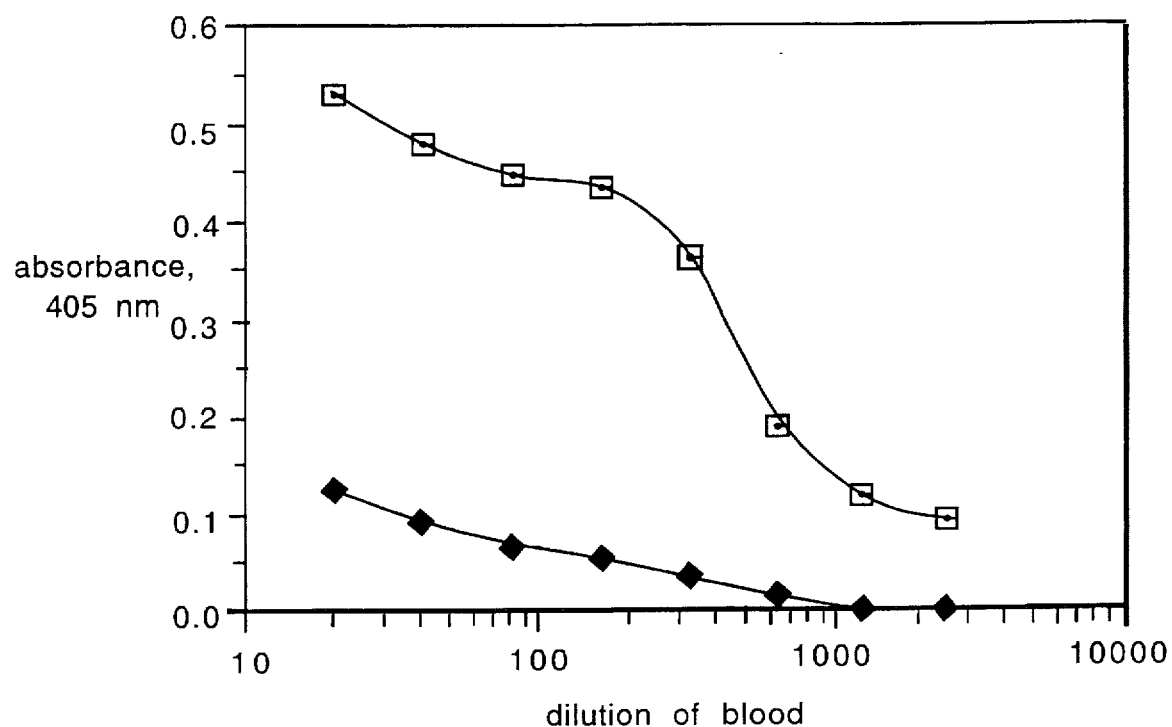
FIG. 4 is a graph of the response to Gd-DTPA of mice injected with Gd-DTPA-BSA (squares) and MPEG(MW 5 kD)-poly1-lysine(MW 53.5 kD)-DTPA(Gd) (diamonds).

Applicants detected the formation of low-avidity, e.g., titer of 800–1,000, of antibodies to DTPA(Gd) in animals injected with BSA-DTPA(Gd) by enzyme-linked immunoadsorbent assay (ELISA), and demonstrated virtually no response in animals injected with compositions of this invention (See FIG. 4). Substantially, no detectable antibodies against DTPA(Gd), acylated polylysine or MPEG were found in animals injected intravenously or intraperitoneally with compositions of this invention 20 days post-injection.

The combination of long-blood half-life and lack of immunogenicity is an important feature of this invention.

Figure 5:
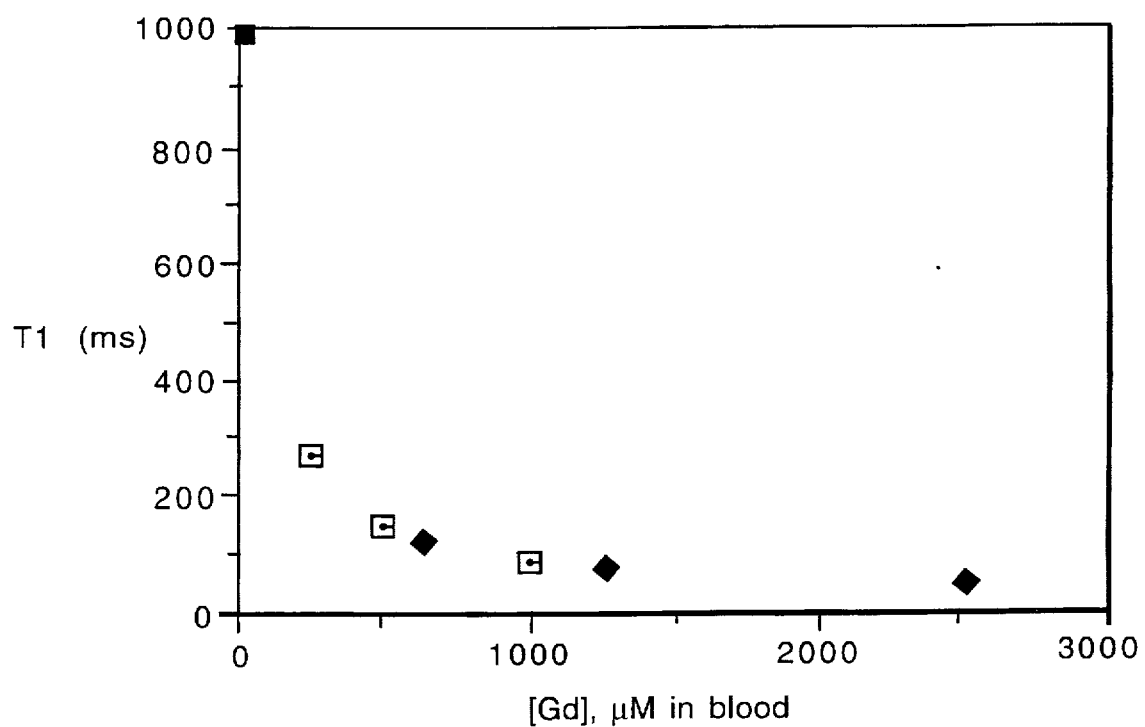
FIG. 5 is a graph of the effect of Gd-labelled MPEG(MW 2 kD)-poly-l-lysine(MW 41 kD)-DTPA (squares) or Gd-labelled MPEG(MW 5 kD)-poly-l-lysine(MW 25 kD)-DTPA (diamonds) on T1 values of blood at various concentrations.

The compositions of this invention have demonstrated a surprisingly high capacity, e.g., up to 13% by weight, for gadolinium and exceptionally high R1/Gd atom, e.g., 20 mM-1 sec-1. Preliminary experiments showed that high-quality angiograms could be obtained when T1 values of blood are decreased at least 5-fold as a result of the injection of the contrast agent. As determined by measuring T1 values in blood, the Gd concentration which allows a 5-fold decrease in T1 corresponds to ca. 300 nmol. Gd/ml of blood (See FIG. 5). In a typical human study this corresponds to an injection of ca. 20 μmol Gd/kg of total body weight, which is 5-fold lower than for Gd-DTPA dimeglumine, which is a frequently used MR contrast agent.

Figure 6:
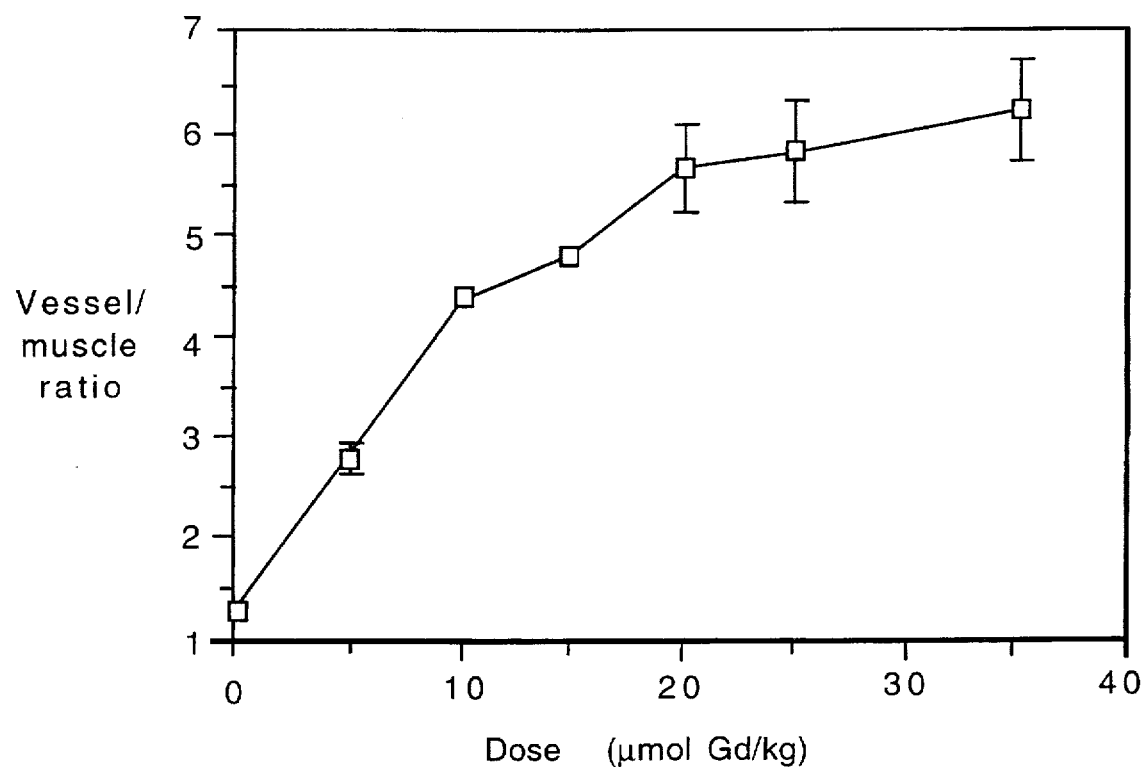
FIG. 6 is a graph of the dose-dependent enhancement of vessels, with the vessel/muscle ratio determined by digitization of signal intensities of several large arteries, e.g., aorta, iliac, and femoral, and nearby muscle tissue.
Figure 7:
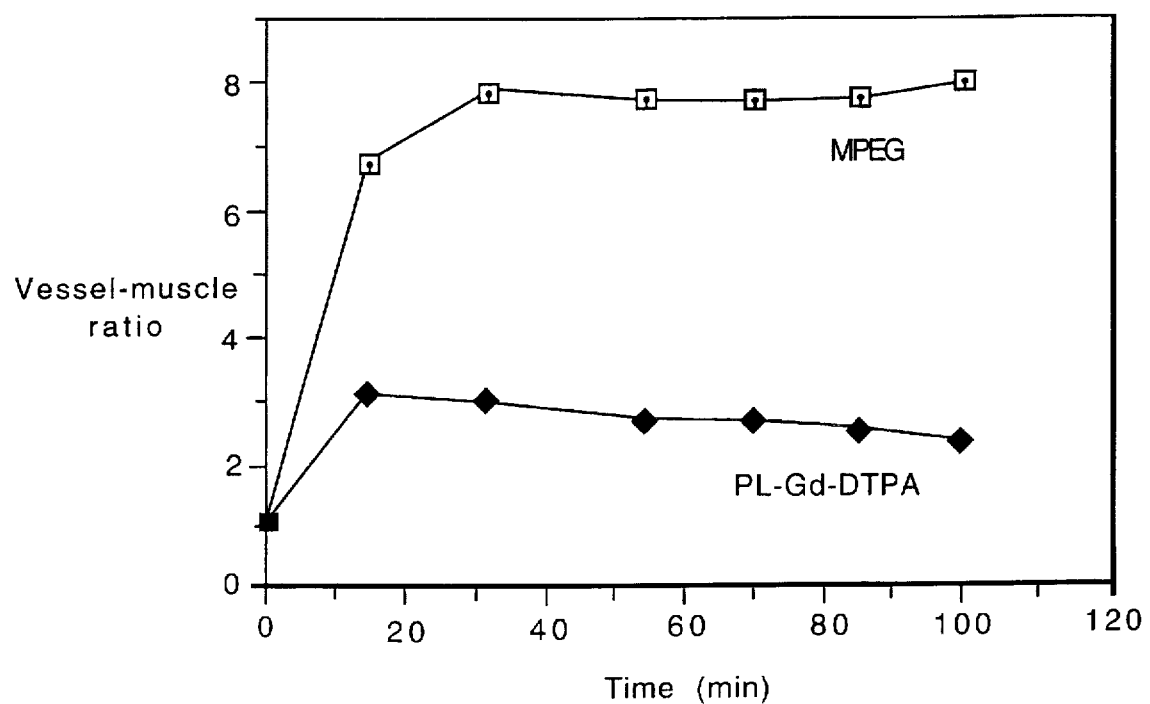
FIG. 7 is a graph of the time-course of a contrast agent in large vessels in a comparative study.

Dose dependence of vessel/muscle signal ratio reveals a plateau at the saturation dose of 20 μmoles of Gd/kg of total body weight (See FIG. 6). At this concentration a contrasted vessel image had a vessel/muscle ratio of 5.5–6, which is a 4-fold increase over previously known preparations administered at a concentration of 50 μmoles Gd/kg total body weight. The compositions of this invention were far superior, i.e., greater than 200%, to poly-l-lysine (MW 25 kD)-DTPA(Gd) in increasing the blood/muscle ratio (See FIG. 7). In this comparative study, rats were injected with 20 μmoles Gd/kg of MPEG(MW 5 kD)- poly-l-lysine (MW 25 kD)-DTPA(Gd) (MPEG squares) or with 50 μmoles Gd/kg of polylysine(MW 25 kD)-DTPA(Gd) (PL-Gd-DTPA, diamonds (See FIG. 7). The increase in vessel/muscle ratio leveled out within 30 minutes and remained constant for the time of observation, which was 100 minutes. Because MPEG(MW 5 kD)-poly-l-lysine(MW 25 kD)-DTPA(Gd) had a higher vessel/muscle ratio, the images of vascular anatomy were considerably better after administering compositions of the invention than after administration of PL-Gd-DTPA.

Figures 8A, 8B:
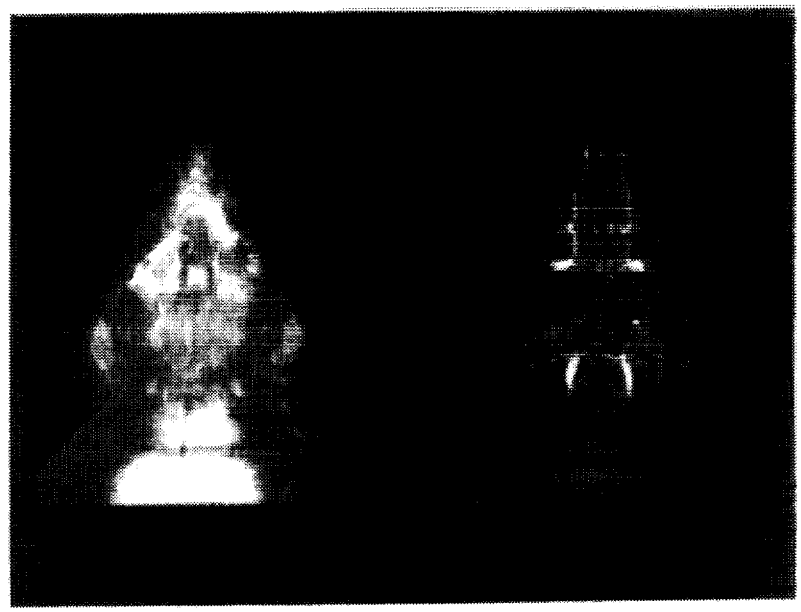
FIGS. 8a and 8b are MR images of the head of a rat in 3-D bright-pixel reconstruction showing the image before (FIG. 8a) and after (FIG. 8b) an intravenous injection of MPEG(MW 5 kD)-poly-l-lysine(MW 25 kD)-DTPA(Gd).

This enabled a dramatic decrease of the dose of Gd required to produce high-quality angiographic images in rats (See FIGS. 8a and 8b). In one study, the MR images of the head of a cat were compared before (See FIG. 8a) and after (See FIG. 8b) intravenously injecting MPEG(MW 5 kD)-poly-1lysine (MW25 kD)-DTPA (Gd) at 30 mol Gd/ml. The images were taken 20 minutes after injection on a Signa (GE Instruments, 1.5 T, 3-TOF SPGR/90 SE 60/6.5 256×192 2NEX) using a 3 inch surface coil. The 3-D bright-pixel reconstructions of vessel maps provided a very high vessel/background signal ratio, eliminating the need for background subtraction. Contrary to known constrast agents, the compositions of the invention injected at 30 μmoles Gd/kg total body weight surprisingly resulted in resolution of submillimeter vessels having an internal diameter of less than 1 mm.

A comparative study between MPEG(MW 5 kD)-poly-1lysine (MW25 kD)-DTPA(Gd) and gadopentate dimeglumine indicated significantly better results for PEG-poly-1lysine (MW25 kD)-DTPA(Gd). In one study, one rat was intravenously injected with MPEG-poly-l-lysine-DTPA(Gd) (20 μmol Gd/Kg total body weight) (left image) and one rat was intravenously injected with gadopentate dimeglumine (100 μmol Gd/kg, from Magnevist®, Berlex Labs) (right image). Immediately, i.e., 10 minutes, following the intravenous administration of Gd-DTPA or the MPEG derivative, the vessel/muscle ratios had increased from 1.4 to 2.7, and 1.4 to 4.5, respectively. Thirty minutes after administration, the ratios were 2.0 for Gd-DTPA and 5.8 for the MPEG(MW 5kD)-poly-l-lysine(MW 25 kD)-DTPA(Gd) at a p-value less than 0.001 (See FIG. 9). Gd-DTPA initially yielded a small increase in vessel contrast. However, as Gd-DTPA is distributed through the extravascular space, contrast is lost. The MPEG derivative compositions of the invention, because of their unique vascular distribution, consistently resulted in high ratios. The images were taken on a Signa using a 5 inch surface coil (See FIG. 9).

Imaging experiments with rabbit and minipig (body weight 40 kg) thorax were performed demonstrating the feasibility of visualizing the pulmonary and coronary arteries using the compositions of this invention (See FIGS. 10a and 10b). In one study, a rabbit was intravenously injected with MPEG(MW 2 kD)-poly-l-lysine(MW 41 kD)-DTPA(Gd) (20 μmol Gd/ml). The images were taken 20 minutes after injection on a Signa using a 5 inch surface coil.

The utility of the compositions of this invention to reveal abnormalities of vessels in experimentally induced pathological conditions was tested in rabbits and rats. By 3-D TOF (Time of Flight) MR angiography the narrowing of the femoral artery at the site of experimental stenosis could be reliably visualized. For visualization of vessel abnormalities in tumor progression, rats with R3230 mammary adeno carcinoma were used. In one study, the MR images of the left flank and thigh of a rat are shown before (See FIG. 11a) and 20 minutes after (See FIG. 11b) an intravenous injection of MPEG (MW 5 kD)-poly-l-lysine(MW 25 kD)-DTPA (Gd) at 20 μmol Gd/ml. The images were taken on a Signa (GE Instruments, 1.5 T, 3-TOF SPGR/60 SE 60/6.5 256×192 2NEX) using a 3 inch surface coil.

Experiments with neoplasia in rats using 20 μmol Gd/kg provided exclusively informative contrast-enhanced angiograms. The location, size, and borders of the tumor and descending veins could be easily recognized on collapsed 3-D MR images. Therefore, the compositions of this invention may be used for detection of both neoplasia and tumor neovascularity which is important in clinical practice for staging and surgical planning.

Additional animal studies using the compositions of the invention were performed to investigate in vivo gamma imaging; biokinetics; immune response; and magnetic resonance imaging.

In vivo gamma-camera imaging

Sprague-Dawley rats (200–250 g) were injected into tail vein using a 26 gauge needle with 1–10 mg/0.5 ml of product I or III, labeled with [$^{111}$In] and Gd, as described in Example 6. Images on a gamma-camera (from Ohio Nuclear) using parallel medium-energy collimator were obtained 30, 60, 120 minutes, and 24 and 70 hours after injection.

Biokinetics of the contrast agent

The Biokinetics of Gd- and [$^{111}$In] labeled product (III or I) was studied using Sprague-Dawley rats ranging from 230–250 g. The animals were injected in the tail vein with 1–10 mg of polymer (60–70 µCi/kg, 2 µm/kg Gd) using a 26 gauge needle under ether anesthesia. Little variation in kinetics was detected within these dose limits. The biodistribution of labeled product was determined in 16 organs, i.e., organ tissues, by measuring radioactivity at each time point indicated on graphs. Two rats were used for each point (See FIG. 3).

Testing of immune response in mice

A 0.2 ml sample of product I (0.5 mmol Gd/kg, i.e. 20-fold imaging dose) was injected intravenously or intraperitoneally into C$_3$H/He mice (n=2). Control animals received BSA-DTPA(Gd) with equal amount of Gd-DTPA, prepared as described in Hnatowich D.J. et al. Science 1979, in the same volume of saline. Animals were observed for 2 weeks for signs of toxicity. No signs of toxicity were detected. After the 2 week period, blood was collected from the tail vein of animals and titer of antibodies was detected by enzyme-linked immunoadsorbent assay (ELISA). ELISA plates were coated with ovalbumin-DTPA(Gd), ovalbumin-MPEG, BSA or acetylated poly-l-lysine (MW 70,000). Only wells of the plate coated with ovalbumin-DTPA(Gd) showed specific binding of mouse immunoglobulins.

MR Imaging

To visualize blood vessels in experimental animals, 0.005–0.05 mmol Gd/kg of product II was injected in male Sprague-Dawley rats (260–360 g) using a 26 gauge butterfly needle in 0.3 ml of sterile saline under barbiturate-induced anesthesia. Appropriate surface coils, 5 inch for two animals and 3 inch for one animal, were applied (See FIGS. 8a and 8b, and FIG. 9).

In experiments with rabbits and minipigs, animals were intubated. Anesthesia was performed with the use of an inhalant Isoflurane. Electrocardiography was constantly monitored. Product II was injected at 0.03 mmol Gd/kg via catheter inserted in the left femoral artery. An extremity surface coil was used for the rabbit studies; a head coil was applied in the minipig studies (See FIGS. 10a and 10b).

In rat studies, 48 saggital slices were imaged on General Electric CSI (thickness=0.7 mm) using a T1-weighted 3D - Time of Flight SPGR pulse sequence (1.5 T, SE 50/6.5, flip angle 60). In rabbit and minipig studies up to 80 slices were imaged (See FIGS. 10a and 10b).

Use of the Compositions as Contrast Agents

The compositions of this invention may be used in medical imaging, and administered intravascularly or by bolus-injection. The vascular images are enhanced due to changes of blood relaxivity or radioactivity. The contrast agents may be used for the improvement of vascular images of large vessels, e.g., arteries and veins, or to visualize small vessels, e.g., submillimeter capillaries. The resolution of the images is increased by providing more detailed information.

The contrast agents may be used for vascular anatomy mapping, determination of vessel stenosis, abnormal vascularity, e.g., neovascularity, normal perfusion, perfusion defects, or functional imaging of the brain.

Use of the Composition as a Therapeutic Agent

The compositions of this invention may also comprise a therapeutic agent, e.g., one or more species of cytostatics, analgetics, antiinflammatory, antiviral, antifungal or psychotropic drugs. The compositions of this invention which include therapeutic agents are beneficial because the prolonged circulation of the composition in the blood substantially prolongs the therapeutic effect of the therapeutic agent. To achieve a therapeutic effect the therapeutic agent should slowly detach or leave the polymeric carrier. This may be achieved by detachably linking or positioning a semi-permeable membrane around the carrier to form a vesicle, allowing the drug concentrated in the vicinity of polymeric carrier to slowly diffuse through the membrane into the intravascular space. The compositions of this invention which include therapeutic agents may be administered intravascularly or by bolus-injection.

The compositions of this invention are described in the following Examples and Experimental section which form embodiments of the present invention and should not be regarded as limiting the scope of invention.

EXAMPLES AND EXPERIMENTAL RESULTS

Example 1

Synthesis of PEG-poly1-lysine (300)-DTPA, Product I

Synthesis of MPEG succinate

Dissolve 6.5 g of MPEG (MW 2000) in 25 ml of peroxide-free dioxane at 60° C. and mix with preheated solution of 1.6 g of succinic anhydride at a 5-fold molar excess in 25 ml of dioxane. Dissolve 300 mg of N,N'-dimethylaminopyridine as a catalyst in 10 ml of dioxane and add to the reaction mixture. Incubate the mixture to at 90° C. for 5 hours. Remove the dioxane by rotary evaporation at 40° C. and dissolve the solid in a minimal amount, e g , 7–10 ml, of methylene chloride, cool to −10° C. and filter on a fritted-glass filter to remove the precipitate of succinic acid. Add 300 ml of ethyl ether per each 5 ml of filtrate and maintain the cloudy solution at −20° C. to precipitate MPEG succinate. Filter the precipitate on a fritted glass filter and wash with ethyl ether.

Dissolve 5.6 g of the dry precipitate with 40 ml of water and pass through an AG 50W X8 resin, (15 g of wet resin, treated with 50% ethanol and deionized water) on a 30-micron fritted glass filter in order to remove the remaining catalyst.

A 5 g sample of MPEG2000 succinate was obtained (86% yield) as a white amorphous solid. The Rf was 0.8 on silica gel 60 TLC plates (from EM Sciences) (developed by a solution of chloroform:methanol:15 mM CaCl2 in a ratio of 65:35:2). The Rf was 0.5 on RP-18 TLC plates (from EM Sciences) in the same system after staining with iodine vapor.

Synthesis of MPEG Succinyl-N-hydroxysuccinimidyl ester

Dissolve the lyophilized MPEG succinate product (2 g, 0.5 mmol) in 10 ml of peroxide-free dioxane, which passed the peroxide-sensitivity test. Sequentially add 0.11 g N-hydroxysuccinimide (Fluka Chemie AG, Buchs, Switzerland) and 0.15 g (0.55 mmol, 1.1 molar excess) of dicyclohexylcarbodiimide (Fluka Chemie AG, Buchs, Switzerland) to the mixture. Stir the reaction mixture for 6 hours at room temperature and cool on ice. Remove dicyclohexylurea by filtration through fritted glass filter or through a GF-C glass wool filter. Remove dioxane on a rotary evaporator, and add 10 ml of methylene chloride and mix with 100 ml of ether under continuous stirring. Store the precipitate at −20° C. overnight. Separate the product by filtration and recrystallize from a dichloroethane:ether mixture at a ratio of 1:9.

Test for an activated ester of MPEG succinate

The percent of the activated ester in solid was determined by solubilizing 1.5 mg of product in anhydrous DMSO (100 μl). Add 10 μl of the solution to 800 μl of 0.05M sodium phosphate (pH 8.5). Record the absorbance at 260 nm for 30 minutes. An increase in absorbance was due to hydrolysis of activated ester (e260 =8260 [mol cm]−1 for N-hydroxysuccinimide at pH 8.5). Approximately 75% of the composition obtained was found to be an activated ester. The Rf was 0.95 on the silica gel 60 (developed by a solution of chloroform:methanol:15 mM CaCl2 at a ratio of 65:35:2) after UV visualization with ammonia fumes.

Synthesis of MPEG-poly-l-lysine-DTPA.

Dissolve 816 mg of poly-l-lysine (PL hydrobromide, MW 67,700 (Sigma Chemical Co), DP: 324 1 1-lysine residues, 25 mM epsilon-aminogroups of 1-lysine, hydrobromide) in 38 ml of 0.1M carbonate buffer (pH 8.7). Dissolve 3.1 g MPEG succinyl hydroxysuccimidyl ester (MPEGOSu, MW 2,200) in 15 ml of dry DMSO. Add the MPEGOSu solution drop-wise to the PL solution with agitation and incubate the mixture for 2 hours under stirring.

The degree of modification was checked by trinitrobenzenesulfonic acid titration, as used in Spadaro, A.C.C. et al., Anal. Biochem. 96:317 (1979). Mix 10 μl of the sample, 100 μl of water, 100 μl of 10% Triton X-100, 100 μl of 0.1M of sodium tetraborate, and 0.35 ml of 2 mg/ml of TNBS in a tube. Incubate for 45 minutes. Stop incubation by addition of 2.3 mg/ml sodium sulfite in 5M $NaH_2PO_4$. The absorbance was determined at 420 nm and compared with that of PL. The amount of modified groups was determined to be equal to 30%.

A suspension of a cyclic anhydride of DTPA (0.5 g/ml in DMSO) was prepared by adding 200 μl portions (1.5 g of cDTPA total) to the solution of PL and MPEG, and the pH was adjusted to 8 with 5N NaOH after each addition. The amount of titratable aminogroups was checked again and no free aminogroups were detected.

Purification of MPEG-poly-l-lysine-DTPA

Dilute the reaction mixture of MPEG-poly-l-lysine-DTPA (MPEG-PL-DTPA) to 300 ml with 0.2M sodium citrate (pH 6.), filter through 0.45 μnylon filter and dialyze in a flow-through cell using a membrane with cut-off of 100 kD (for globular proteins). Concentrate to 30–50 ml and dilute to 300 ml with citrate. Repeat the procedure 2 times using water instead of citrate in the last stage. Concentrate the solution to 15 ml, and lyophilize. Alternatively, the sample may be filtered through sterile 0.2 μm membrane and stored at 4° C. A table of the theoretical and actual chemical analysis is presented below:

Chemical analysis:
Theoretical % C 46.7, %H 7.0, %N 8.0
Actual % C 41.2, %H 6.4, %N 9.7

Example 2:

Synthesis of MPEG(MW 5 kD)-poly-l-lysine (MW 25 kD)-DTPA, Product II

Synthesis of MPEG succinate

Dissolve 40 g of MPEG (MW 5000) in 250 ml of peroxide-free dioxane at 60° C. and mix with a preheated solution of 8 g of succinic anhydride (10-fold molar excess) in 50 ml of dioxane. Dissolve 900 mg of N,N'-dimethylaminopyridine as a catalyst in 10 ml of dioxane and add to the reaction mixture. Incubate the mixture at 90° C. for 8 hours.

Remove the dioxane by rotary evaporation at 40° C., and dissolve the solid in 20 ml of methylene chloride, cool to −10° C., and filter on a fritted-glass filter to remove the precipitate of succinic acid. Add 300 ml of ethyl ether per each 10 ml of filtrate and precipitate the cloudy solution of MPEG at −20° C. succinate. Filter the precipitate on a fritted glass filter (10–20 μ, Corning) and wash with cold ethyl ether.

Dilute 35 g of the dry precipitate with 100 ml of water and pass through AG 50W X8 resin (25 g of wet resin, treated with 50% ethanol and deionized water) on a 100-micron glass filter in order to remove the remaining catalyst. In order to reduce the amount contaminating peroxides, treat the solution of MPEG2000 succinate in water with 10 mM sodium borohydride for 4 hours at room temperature. Lyophilize the solution, redissolve the solution in methylene chloride (0.1 g/ml), and resediment the solution with the addition of diethyl ether. A 30 g sample of MPEG5000 succinate sample was obtained (an 83% yield) as white amorphous solid. The Rf was 0.5 on RP-18 TLC plates (from EM Sciences) (developed in a solution of chloroform:ethanol:water at a ratio of 65:25:4) after staining with iodine vapor.

Synthesis of MPEG succinyl-N-hydroxysuccinimidyl ester

Dissolve 5.29 g (1 mmol) of the lyophilized MPEG succinate product in 40 ml of peroxide-free tetrahydrofurane, which passed peroxide-sensitive test, and add 0.17 g N-hydroxysuccinimide (1.5 mmol, Fluka Chemie AG, Buchs, Switzerland) and 0.3 g (1.1 mmol) of dicyclohexylcarbodiimide (Fluka). Stir the reaction mixture for 6 hours at room temperature and then cool on ice. Remove the dicyclohexylurea by filtration through a fritted glass filter (20–30 μ, Corning). Remove the tetrahydrofurane on a rotary evaporator, add 10 ml of methylene chloride and mix with 100 ml of ether under continuous stirring. Precipitate at −20° C. overnight. Separate the product by filtration and recrystallize from a dichloroethane:ether mixture at a ratio of 1:9.

Test for an activated ester of MPEG succinate

The percent of the activated ester in solid obtained was determined as described in Example 1.

Synthesis of PEG-poly-1-lysine-DTPA

Dissolve 620 mg of poly-l-lysine (PL hydrobromide, MW 41,100, (Sigma Chemical Co.) DP: 196 1-lysine residues, 25 mM epsilon-aminogroups of 1-lysine, hydrobromide) in 112 ml of 0.1M carbonate buffer(pH 8.7). Dissolve 2.9 g methoxy polyethylene glycolsuccinyl hydroxysuccimidyl ester (MPEGOSu, MW 5,200) in 5 ml of dry DMSO. Add the PEGOSu solution drop-wise to the PL solution under agitation and incubate the mixture for 2 hours under stirring. Check the degree of modification by trinitrobenzenesulfonic acid titration as described in Example 1.

Prepare a suspension of cyclic anhydride of DTPA ( 0.5 g/ml in DMSO) by adding 200 μl portions (1.5 g of cDTPA total) to the solution of MPEG-PL and adjust the pH to 8 with 5N NaOH after each addition. Alternatively, the solution may be prepared by mixing of 2.5 mmol of DTPA, 0.5 mmol N-hydroxysulfosuccinimide (pH 4) and 0.5 mmol ethyl diaminopropylcarbodiimide in 50 ml of water. The solution is then mixed for 3 min and added to the mixture the solution of MPEG-PL (pH 8). Check the amount of titratable aminogroups. (No titratable amino groups were detected).

Purification of MPEG-PL-DTPA

Dilute the reaction mixture to 300 ml with 0.2M sodium citrate (pH 6), filter through 0.45 μ nylon filter, and dialyze in a flow-through cell using a membrane with a cut-off of 50 kD (for globular proteins). Concentrate to 30–50 ml and dilute to 300 ml with citrate. Repeat the procedure 2 times using water instead of citrate at the last stage. Concentrate the solution to 15 ml, and lyophilize. Alternatively, filter the sample through a sterile 0.2 μm membrane and store at 4° C. A table of the theoretical and actual chemical analysis is presented below:

Chemical analysis
 Theoretical %C 51.2, %H 8.2, %N 2.7
 Actual %C 46.4, %H 7.8, %N 3.7

Example 3

Synthesis of MPEG-poly-l-lysine(MW 67 kD),DTPA, Product III

Prepare according to the procedures of Example 1, using poly-l-lysine with a mean MW of 110,000.

Example 4

Synthesis of MPEG-poly-l-lysine (MW 53.5 kD)-DTPA, Product IV

Prepare according to the procedures Examples 1 and 2, using poly-l-lysine with a mean MW of 87,400 and MPEG (MW 5000)succinyl succinate.

Example 5

Synthesis of MPEG-poly-l-lysine(69)-(dithio)propionylpoly-l-lysine-DTPA, Product V Dissolve 50 mg of N-e-benzoyloxycarbonyl-poly-1lysine in 3 ml of dimethylformamide and treat with 10 mg of N-succinimidyl 3-(2-pyridyldithio)propionate in the presence of 20 μl of triethylamine. Incubate the product overnight and precipitate by the addition of 20 ml of water. Freeze-dry the precipitated product and divide into two equal parts. Redissolve the first part in dimethylformamide (0.5 ml) and treat for 20 minutes with 10 mM beta-mercaptoethanol, and precipitate by adding 10 ml of nitrogen-saturated water and freeze-dry. Redissolve this product together with the second part of the compound in 2 ml of dimethylformamide and add 5 μl triethylamine. Stir the mixture at room temperature overnight. Precipitate the product and wash with water, then redissolve the product in 1 ml of an HBr in glacial acetic acid solution, incubate for 1 hour, and mix with 20 ml of distilled ethyl ether. Wash the precipitate with ether and convert into MPEG-derivative and then into MPEG-DTPA derivative as described in Example 1, using DMFA instead of DMSO for solubilization of MPEG-succinyl succinate and DTPA cyclic anhydride.

Example 6

Preparation of [$^{111}$In]-labeled products I, II, III or IV

Prepare 100–500 μl of [111 In] citrate solution (pH 4.5) with total activity of 30–500 μCi. Dissolve 1 mg of products I, II, III or IV as prepared above in Citrate Balance Saline (CBS) of 10 mM citrate, 0.15M NaCl (pH 6.6). Mix the solutions and incubate for 30 minutes at room temperature. Purify by dialysis against 4 changes of 100 ml of the CBS. The dialyzed product was found to incorporate 98–100% of the radioactivity.

Example 7

Preparation of gadolinium labeled products I, II, III or IV

Prepare a 100 ml of 20 mM solution of $GdCl_3$ in 0.2M citrate (pH 5.5). Dissolve 0.1–100 mg of products I, II, III or IV in 1–5 ml of water and place in dialysis bags with pores small enough to retain molecules larger than 10 kD. Place the dialysis bags in the Gd-citrate solution for 8–10 hours. Then substitute the Gd-citrate solution by 0.2 M citrate and, finally, with 10 mM citrate-balanced saline (osmolarity is 300 mOsm). Sterile-filter or lyophilize the Gadolinium-labeled products.

Example 8

Preparation Of [$^{111}$In] and gadolinium-labeled products I, II, III or IV

Prepare according to the procedures of Example 4 and then transfer the dialysis bags to Gd-citrate solution as described in Example 7.

Example 9

The purification of labeled product I, II, III or IV

A solution of gadolinium or [$^{111}$In] and gadolinium labeled products was prepared at 50–100 mg of polymer/ml of 5 mM sodium citrate (pH 6). Load the solution on a column of Sephadex A-25 (1×40 ml, 5 mM citrate, pH 6) and elute non-bound material with the same buffer, which has been collected, dialyzed against water, and lyophilized.

Although the above examples present general and specific guidelines for preparing and using contrast agents of this invention, one skilled in the art can assemble additional candidate molecules and compare their characteristics to those claimed by the invention.

Experimental characterization of products Determination of size

The apparent hydrodynamic radii were determined using gel-filtration on an Ultragel AcA-34 (from LKB-IBF, France) column (1×40 ml) and LALLS (Submicron Particle Analyzer N-4MD from Coulter, Hialeah, Fla.).

Solutions of products I-IV in Gd-labeled form were prepared at 1 mg of polymer/ml and the sizes were determined by Size Distribution Processor (SDP) weight analysis at 90° angle scattering before and after the formation of Gd complexes (See Table 1). The calculation of molecular weights was based on determination of the degree of modification of PL with MPEG, as described in Example 1, assuming that on the second stage of modification all aminogroups were substituted with DTPA.

TABLE 1

| | Determination of size and molecular weights | | | |
|---|---|---|---|---|
| Product | diameter (LALLS) | MW (LALLS) | Apparent MW (AcA34)* | Calculated MW |
| I | 15.5 ± 1 nm | 171 kD | 200 kD | 417 kD |
| II | 16.4 ± 4 nm | 150 kD | 280 kD | 412 kD |
| III | 38.1 ± 10.5 nm | ND | >380 kD | 860 kD |
| IV | 53 ± 12 nm | ND | >380 kD | 960 kD |

Note:
AcA 34 column was precalibrated with globular protein molecular weight markers;
ND: No Data available.

Determination of Gd content

The Gd content was determined titrametrically, (as in Korbl, J. and Pribil, R., Chemist-Analyst 45:101–103 (1956), or by plasma emission spectroscopy (from Gallbraith Labs, Knoxville Tenn.). The Gd content did not exceed 13.18% by weight (0.8 mmol Gd/g polymer, product I). Typically products II, III, and IV contained ca. 5% Gd by weight (0.32 mmol Gd/g polymer).

Measurement of relaxivity values (R1 and R2)

Determination of relaxation times of the $H_2O$ protons was performed using a Minispec (IBM PC/20) pulsed NMR spectrometer at 20MHz, 38° C. Gd-labeled products were appropriately diluted with CBS and T1 and T2 parameters were measured. Inversion recovery and CPMG pulse sequences were used to determine T1 and T2 values, respectively. The concentration dependencies of relaxation rates 1/T1 and 1/T2 were plotted and fitted using linear regression (r=0.99). R1 and R2 values were determined as slope values (See Table 2).

TABLE 2

| Product | Molecular and atomic relaxivities | | | | [mMol-1 s-1] |
|---|---|---|---|---|---|
| | R1 | R2 | R1/Gd | R2/Gd | |
| I | 5061 | 5053 | 18.1 | 16.9 | |
| II | 2076 | 2035 | 17.6 | 17.1 | |
| IV | 4565 | 6547 | 18.5 | 19.0 | |

Calculated values of molecular weights of Gd-labeled products were used for molecular relaxivity determinations.

Other embodiments are within the following claims:

What is claimed is:

1. A biocompatible medical composition comprising:

a non-polysaccharide polymeric carrier;

a plurality of protective chains linked to said polymeric carrier, wherein each protective chain is at least 500 Daltons; and a reporter group linked to said carrier and not linked to said protective chain, wherein said reporter group is a complexone or a therapeutic agent, and both said carrier and said reporter group are protected by said protective chains from contact with macromolecules other than in said composition.

2. The composition of claim 1, wherein said polymeric carrier is chosen from the group of polyamino acids, polyethyleneimines, natural saccharides, aminated polysaccharides, aminated oligosaccharides, polyamidoamine, polyacrylic acids, or polyalcohols.

3. The composition of claim 2, wherein said polyamino acid has 20–560 amino acid units.

4. The composition of claim 3, wherein said polyamino acid has a molecular weight of 1,000–100,000 daltons.

5. The composition of claim 2, wherein said polyamino acid is a polymer of a single species of amino acid.

6. The composition of claim 2, wherein said polyamino acid is a polymer of at least two different species of amino acids.

7. The composition of claim 2, wherein said polyamino acid is a block copolymer.

8. The composition of claim 2, wherein said polyamino acid comprises polyamino acid fragments linked by cleavable bonds.

9. The composition of claim 8, wherein said cleavable bonds are S—S bonds.

10. The composition of claim 2, wherein said polyamino acid is poly-l-lysine, poly-d-lysine, poly-alpha, beta-(2-aminoethyl)-D,L aspartamide, or poly-l-aspartic acid.

11. The composition of claim 2, wherein said polyamino acid is non-proteinaceous.

12. The composition of claim 1, wherein said protective chain is polyethylene glycol, methoxypolyethylene glycol, methoxypolypropylene glycol, a copolymer of polyethylene glycol, methoxypolyethylene glycol, or methoxypolypropylene glycol, or derivatives thereof.

13. The composition of claim 1, wherein said protective chain is a block copolymer of polyethylene glycol and one of the group of polyamino acids, polysaccharides, polyamidoamines, polyethyleneamines, or polynucleotides.

14. The composition of claim 1, wherein said protective chain is a copolymer of polyethylene glycol comprising a monoester of a dicarboxylic acid.

15. The composition of claim 1, wherein said protective chain has a molecular weight of 500–10,000 daltons.

16. The composition of claim 1, wherein said complexone is a chelating group.

17. The composition of claim 16, wherein said chelating group is diethylenetriamine-pentaacetic acid, triethylenetetraminehexaacetic acid, ethylenediaminetetraacetic acid, 1,2-diaminocyclo-hexane-N,N,N',N'-tetraacetic acid, N,N'-Di(2-hydroxybenzyl)ethylenediamine, N-(2-hydroxyethyl)ethylenediaminetriacetic acid, nitrilotriacetic acid, ethylene-bis(oxyethylene-nitrilo)tetraacetic acid, 1,4,7,10,-tetraazacyclodo-decane-N,N',N'',N''',-tetraacetic acid, 1,4,7,10,-tetraazacyclododecane -N,N',N''-triacetic acid, 1,4,7-tris(carboxymethyl)-10-(2-hydroxy)propyl)-1,4,7,10-te traazocyclodecane, 1,4,7-triazacyclonane-N,N',N''-triacetic acid, or 1,4,8,11-tetraazacyclotetradecane-N,N',N'', N'''-tetra-acetic acid.

18. The composition of claim 1, wherein said complexone is linked to a diagnostic agent.

19. The composition of claim 18, wherein said diagnostic agent is a contrast agent.

20. The composition of claim 19, wherein said contrast agent comprises a paramagnetic element.

21. The composition of claim 20, wherein said paramagnetic element is chosen from the group of transitional metals or lanthanides having atomic numbers 21–29, 42, 44, or 57–71.

22. The composition of claim 20, wherein said paramagnetic element is gadolinium (III), dysprosium (III), holmium (III), europium (III), iron (III), or manganese (II).

23. The composition of claim 1, further comprising an alfa-, beta-, or gamma-emitting radionuclide linked to said complexone.

24. The composition of claim 23, wherein said radionuclide is gallium 67, indium 111, technetium 99m, chromium 51, cobalt 57, molybdenum 99, or a molecule linked to an iodine isotope.

25. The composition of claim 19, wherein said contrast agent comprises a superparamagnetic element.

26. The composition of claim 20, wherein said contrast agent further comprises a radionuclide.

27. The composition of claim 1, wherein said therapeutic agent is a cytostatic, antibiotic, hormonal, analgesic, psychotropic, anti-inflammatory, antiviral, or antifungal drug, or a lymphokine.

28. The composition of claim 1, further comprising a targeting group linked to said polymeric carrier.

29. The composition,of claim 28, wherein said targeting group is an antibody, fragment of an antibody, chimeric, antibody, enzyme, lectin, or saccharide ligand.

30. The composition of claim 1, having the formula:

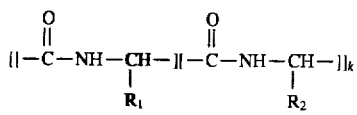

wherein said

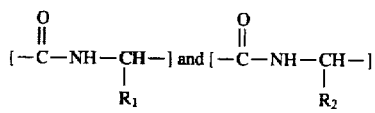

groups can be linked in any order; wherein k is 100–560; $R_1$ is $(CH_2)_4NHCO(CH_2)_nCOOCH_2CH_2A$-B-$OR_3$, where n is 2–6; A is $[OCH_2CH_2]_x$, where x is 15–220; B is $[OCH_2CH_2]_x$ or $[OCH(CH_3)CH_2]_y$, where y+x is 17–220; $R_2$ is a chelating group; and $R_3$ is H, $(CH_2)_pCH_3$ or $(CH_2)_pCOOH$, and p is 0–7.

31. The composition of claim 30, wherein said chelating group is diethylenetriamine pentaacetic acid, 1,4,7,10,-tetraazacyclododecane-N,N',N", N"'-tetraacetic acid, 1,4,7,10,-tetraazacyclododecane-N,N',N",-triacetic acid, ethylenebis(oxyethylenenitrilo)tetraacetic acid, or ethylenediaminetetraacetic acid.

32. The composition of claim 18, wherein said diagnostic agent is a fluorine-containing molecule.

* * * * *